United States Patent [19]

Weetall

[11] 4,166,765

[45] Sep. 4, 1979

[54] DETECTING NEISSERIA BACTERIA

[75] Inventor: Howard H. Weetall, Big Flats, N.Y.

[73] Assignee: Corning Glass Works, Corning, N.Y.

[21] Appl. No.: 837,366

[22] Filed: Sep. 28, 1977

[51] Int. Cl.$^2$ .............................................. C12K 1/06
[52] U.S. Cl. ....................................... 435/26; 435/37; 435/871
[58] Field of Search ................. 195/103.5 R, 103.5 M

[56] References Cited

U.S. PATENT DOCUMENTS

| 3,415,718 | 12/1968 | Forkman et al. | 195/103.5 M |
| 3,930,956 | 1/1976 | Juni | 195/103.5 M |
| 4,039,387 | 8/1977 | Simpson et al. | 195/103.5 M |

*Primary Examiner*—Alvin E. Tanenholtz
*Attorney, Agent, or Firm*—Clinton S. Janes, Jr.; Clarence R. Patty, Jr.; William E. Maycock

[57] ABSTRACT

Bacteria of the genus Neisseria can be detected in a sample by testing for the presence of an enzyme capable of oxidizing 1,2-propanediol and reducing NAD (nicotinamide-adenine-dinucleotide). The complete structure of the enzyme is not known but, because of those two characterizing properties, the nomenclature 1,2-propanediol dehydrogenase therefor is proposed herein.

8 Claims, No Drawings

DETECTING NEISSERIA BACTERIA

RELATED APPLICATIONS

Patent application Ser. No. 837,365, now U.S. Pat. No. 4,111,752, filed of even date by the present applicant entitled "Comparative Test for Neisseria", patent application Ser. No. 837,364, filed of even date by the present applicant entitled "Detection of Neisseria Bacteria by Immunoassay", patent application Ser. No. 837,363, filed of even date by the present applicant entitled "Immunoassay of Neisseria Bacteria Via $(NH_4)_2SO_4$ Precipitation", patent application Ser. No. 837,360, filed of even date by H. C. McDonald entitled "Detection and Quantitation of Neisseria Via Radioimmunoassay of an Enzyme Present in Neisseria Bacteria", patent application Ser. No. 837,362, filed of even date by the present applicant entitled "Immunological Detection of Neisseria Bacteria Via Labelled Antibodies", and patent application Ser. No. 837,361, filed of even date by M. M. Takeguchi and the present applicant entitled "Transport System for Clinical Specimens". Each of those applications is assigned to the assignee of the present application.

BACKGROUND OF THE INVENTION

This disclosure is concerned generally with tests for determining the presence of certain microorganisms and specifically with a test for detecting Neisseria bacteria via a simple enzymatic reaction.

The importance of being able to quickly and accurately detect the presence of Neisseria bacteria, especially *Neisseria gonorrhoeae*, is well recognized. Present tests for detecting the presence of organisms such as *N. gonorrhoeae* include the preparation of bacteria cultures or the use of serological methods. Such tests, however, have known limitations. See, for example, the publication, "International Symposium on Gonorrhea", B. B. Diena, Ed., a collection of papers presented at the October, 1973 International Symposium on Gonorrhea sponsored by the Health Protection Branch, Health and Welfare Canada, Ottawa, especially at p. 34 et. seq. Quite surprisingly, a relatively simple and quick enzymatic test for the presence of Neisseria has been discovered. The test offers many advantages over currently used methods. Details are disclosed herein.

SUMMARY OF THE INVENTION

The method for detecting the presence of bacteria of the genus Neisseria in a fluid sample comprises testing the sample for the presence of a particular enzyme, this enzyme having the capability of oxidizing 1,2-propanediol and reducing nicotinamide-adenine-dinucleotide (NAD). The structure of the enzyme is not fully understood and no identification thereof in the literature is known. However, because of those two characterizing properties, the name 1,2-propanediol hydrogenase is proposed therefor and will be utilized in describing the present inventive method.

In one embodiment of the invention, the method comprises incubating a lysate of body fluid or exudate in the presence of 1,2-propanediol and NAD, and determining whether the cofactor NAD is reduced to NADH by monitoring any change in molar concentration of NADH. Such change can be determined fluorometrically (by noting any increase in fluorescence at 460 nm when excited at 340 nm) or spectrophotometrically (by noting any increase in molar absorbency at 340 nm).

In preferred embodiments, the NADH concentration is determined fluorometrically. The test permits the detection of bacteria in a sample containing as few as $2.0 \times 10^2$ organisms.

SPECIFIC EMBODIMENTS

Since the present disclosure is based on detecting the presence or absence of an enzyme specific to the bacterial genus Neisseria, it can be appreciated that a variety of methods for detecting the enzyme will become apparent in view of this disclosure. In the illustrative examples below, enzymatic activity of 1,2-propanediol dehydrogenase, indicative of Neisseria, was easily detected by monitoring any change in NADH concentration due to the reduction of cofactor NAD to NADH in the presence of the specific substrate 1,2-propandiol. Under the reaction (incubation) conditions used in our examples and test, an increase in NADH concentration, observed fluorometrically at 460 nm (stimulated at 340 nm) or as a spectrophotometric increase in molar absorbence at 340 nm, could occur only if the sample being tested included the enzyme 1,2-propanediol dehydrogenase since the only "substrates" offered to the sample were the NAD and 1,2-propanediol.

Although it is thought that the presence of the specific enzyme can be detected in a variety of ways, our preferred method, based on convenience, availability of equipment, and practicality, involves two basic steps. In the first step a lysate of the sample is prepared. In the second step, the lysate is incubated in the presence of an aqueous solution of NAD and 1,2-propanediol.

Preparation of the lysate can be accomplished by known means using known lysing agents or solutions. Since the purpose of the lysing step is to break down cellular walls causing the release of intracellular contents such as the 1,2-propanediol dehydrogenase (if present), any known means for accomplishing this result can be used so long as it does not interfere with the subsequent enzymatic assay. A suitable lysate can be prepared by simply suspending the cells of a sample or specimen in the various TRIS buffers or lysozyme solutions described below. In some cases, depending upon the sample source and other factors, it may be desirable to add a small amount of a chelating agent (e.g., EDTA) to complex with any divalent metal ions in the lysate which might interfere with the test for enzymatic activity. Because of the sensitivity of the test, the presence of Neisseria can be detected in a lysate prepared sample containing as few as $2 \times 10^2$ or less of the Neisseria. Being able to prepare a useable lysate from such a small number of cells offers obvious advantages in that it permits an effective test for Neisseria even in cases where the initial specimen is relatively small (e.g., from a swab population).

After the lysate is prepared, it, or a part of it, is incubated in the presence of a buffered aqueous solution of NAD and 1,2-propanediol. As used herein the expressions incubated, incubation, or the equivalent, refer to those reaction conditions sufficient to cause the oxidation of 1,2-propanediol and the reduction of NAD by the lysate sample if the enzyme 1,2-propanediol dehydrogenase is present.

Initially, six organisms were tested for enzymatic activity toward the NAD and 1,2-propanediol solution. These organisms were:
*Proteus mirabilis*
Enterococci

*Escherichia coli*
*Staphylococcus aureus*
*Neisseria gonorrhoeae*-Types 3 and 4
*Staphylococcus epidermidis*

Only the *N. gonorrhoeae* was found to have detectable levels of the specific enzymatic activity. In a subsequent experiment two more Neisseria species were similarly tested to determine if the enzyme was genus specific or merely species specific to *N. gonorrhoeae*. The added species tested were:

*N. meningitidis*
"*N. catarrhalis*"

Surprisingly, only the *N. meningitidis* demonstrated the enzymatic activity toward the NAD and 1,2-propanediol. Later, it was found that the *N. catarrhalis* had been placed in the wrong genus and is now properly classified as *Branhamella catarrhalis*. To confirm that the enzyme system might be specific to the genus Neisseria, three more species were similarly tested:

*N. lactamicus*
*N. subflava*
*N. flavescens*

The lysates of all three were found to have the enzymatic activity of 1,2-propanediol dehydrogenase. To further test the hypothesis that the enzyme was genus specific to Neisseria, sixteen additional samples of materials were similarly tested with negative results. Many of the materials tested included cells or organisms of the type associated with a specimen sample (e.g., cervical swab) commonly used to test for the presence of Neisseria, especially *N. gonorrhoeae*. The results of these tests and the previous tests are summarized in Table I.

TABLE I

| Material or Organism Tested | Enzyme Present Yes (+), No (−) |
|---|---|
| *Neisseria gonorrhoeae* | + |
| *Neisseria meningitidis* | + |
| *Neisseria lactamicus* | + |
| *Neisseria subflava* | + |
| *Neisseria flavescens* | + |
| "*Neisseria*" *catarrhalis**  | − |
| *Lactobacillus acidophilus* | − |
| *Candida albicans* | − |
| *Haemophilus vaginalis* | − |
| *Staphylococcus aureus* | − |
| *Staphylococcus epidermidis* | − |
| *Enterococci* | − |
| *Escherichia coli* | − |
| *Enterobacter cloacae* | − |
| *Proteus mirabilis* | − |
| *Klebsiella pheumonial* | − |
| *Beta-Streptococci*, GP. B | − |
| *Acinetobactor calcoaceticus* | − |
| *Trichomonas vaginalis* (protozoan) | − |
| Red Blood Cells | − |
| Epithelial Cells | − |
| Polymorphonuclear leucocytes (PMN) | − |
| Leucocytes (lymphocytes) | − |
| Human Serum | − |
| Calf Serum | − |
| Rabbit Serum | − |

*Actually *Branhamella catarrhalis*

Detailed examples of the representative assays are described below.

ASSAY PROCEDURE

I. Lysate Preparation

Suspensions of various bacteria (*N. gonorrhoeae* type 3,4, *S. aureus*, *S. epidermidis*, *P. mirabilis*, *Enterococci* and *E. coli*) were prepared in 0.03 M TRIS buffer, pH 9.0. The suspensions were prepared so as to contain approximately $10^5$ bacteria (determined by an absorbency of 0.1 on a Spec 20 spectrophotometer). Five milliliters of each bacterial suspension were prepared and to each suspension was added 0.5 ml of a 0.1% solution of egg-white lysozyme (Biozyme Laboratories) prepared in 0.03 M TRIS buffer, pH 9.0. This mixture of bacteria-buffer-lysozyme was mixed briefly and allowed to sit two minutes at room temperature. EDTA (ethylenediamine tetraacetic acid) was added next as 0.5 ml of a 0.1% solution in 0.03 M TRIS buffer, pH 9.0. The tubes containing the bacteria, EDTA, and lysozyme were then agitated in a shaker bath for 10 minutes (12 reciprocating cycles/5 sec.).

These solutions were spun at 5,000 rpm for ten minutes and the supernatants decanted off of the "buttons". This supernatant was the bacterial lysate.

II. Assay Conditions

The following reagents were added to 12×75 mm plastic tubes:

| | |
|---|---|
| NAD | - 10 mg/ml in 0.1M TRIS buffer, pH 9.0 |
| | - add 100 μl/tube |
| TRIS buffer | - 0.1M, pH 9.0 |
| | - add 2.85 ml/tube |
| 1,2-propanediol | - add 50 μl (pure)/tube |

To each test tube was added 100 μl of a bacterial lysate. Incubations varied in time from being read immediately and continuously for 4 minutes, to allowing the assay tubes to incubate one-half hour before reading. All procedures and incubations were carried out at room temperature.

The samples were read at 340 nm (ultraviolet) on a Perkin-Elmer double beam spectrophotometer. A Honeywell Electronik 194 recorder was used to record absorbency. The tests that were read immediately and continuously for 4 minutes were allowed to record for the same time period. Those tests read after 30 minutes were not read continuously, but had their absorbencies recorded after the incubation period [Activity (A) was determined in the 4 minute monitored assay and in the 30 minute assay].

III. Assay Results

A. After four minutes of incubation and thirty minutes of incubation, *no* bacterial lysate tested showed any enzyme activity (increased absorbency) except for *N. gonorrhoeae*. See Table II.

B. A dilution of the lysate was taken such that if all the bacterial had lysed, one would have the equivalent of $2 \times 10^{-10}$ g. of bacteria. This represents approximately 200 bacteria.

C. Enzymatic activity: This was determined using the formula:

$$\text{units/mg protein} = \frac{\Delta A/\text{min.} \times .161}{\text{mg. ENZ/ml reaction mixture}}$$

This activity was determined to be 0.268 units/mg protein for the 4 minute incubation and 0.322 units/mg protein for the 30 minute incubation. However, it should be appreciated that a large percentage of the protein represents the added lysozyme.

D. This enzyme activity of the lysate was determined to remain essentially unchanged for at least 12 days at 0° C. when stored undiluted.

The results of these initial experiments are summarized as follows:

TABLE II

| Bacteria | ΔA/ 4 Min. | ΔA/ 30 Min. | Enzymatic Activity 4 Min. Incub. | Enzymatic Activity 30 Min. Incub. |
|---|---|---|---|---|
| P. mirabilis | 0 | 0 | 0 | 0 |
| Enterococci | 0 | 0 | 0 | 0 |
| E. coli | 0 | 0 | 0 | 0 |
| S. aureus | 0 | 0 | 0 | 0 |
| N. gonorrhoeae-3,4 | 0.01 | 0.36 | 0.268 units/mg. protein | 0.322 units/mg protein |
| S. epidermidis | 0 | 0 | 0 | 0 |

Further Tests

Five additional organisms were grown upon five plates each. These were washed off with 20 ml TRIS buffer, pH 8.0, and lysed in ice water containing 0.1% lysozyme and 0.1% EDTA. The extracts were assayed for enzyme activity using NAD (10 mg/ml) and 1,2-propanediol as follows:

0.1 ml lysate
2.75 ml 0.1 M TRIS, pH 9.0
100 μl NAD
50 μl 1,2-propanediol

The results are summarized in Table III.

TABLE III

| Organisms | Units of Act./ml | Remarks |
|---|---|---|
| N. meningitidis | 25 | Cloudy |
| 1:10 dilution | 2.7 | |
| "N. catarrhalis" | 0 | Clear (complete lysis) |
| S. aureus | 0 | Cloudy |
| S. epidirmus | 0 | Cloudy |
| E. coli | 0 | Cloudy |

In yet further work, the enzyme of the N. meningitidis lysate was shown to be immunologically similar to the enzyme of the N. gonorrhoeae lysate. Antibodies (Ab) to the 1,2-propanediol dehydrogenase were developed by using known techniques. The N. meningitidis which showed the enzyme activity was tested with that antisera (titer 1:4) by adding 0.1 ml of the lysate to 0.1 ml whole serum. The addition was incubated for 60 minutes and assayed for enzyme activity. Then the specific anti-enzyme antibody was added to determine percent inhibition of enzyme activity. The results are summarized in Table IV.

TABLE IV

| Sample | Ab added | Units of Activity | % Inhibition |
|---|---|---|---|
| Undiluted | None | 30 | 0 |
| Undiluted | 0.1 ml | 16 | 46.5 |
| 1:10 | None | 2.7 | 0 |
| 1:10 | 0.1 ml | 0.2 | 92.5 |

The N. meningitidis was inhibited by the antibody indicating that the organism not only contained an enzyme like the N. gonorrhoeae, but it also immunologically cross-reacts as regards the immunological specificity of the two enzymes.

To have a basis for comparing our enzymatic method with conventional culturing techniques used to detect the presence of N. gonorrhoeae, twenty clinical samples were tested for that organism by the inventive method (fluorometrically) and via a conventional culturing method. The fluorometric readout used in the inventive method was recorded in units of increased fluorescence (ΔF). The results are summarized in Table V.

TABLE V

| | | Comparison with Culture Method | |
|---|---|---|---|
| Sample No. | ΔF Units | Yes (+), No (−) Enzymatic Method | Culture Method |
| 1 | 5 | − | − |
| 2 | 39 | + | + |
| 3 | 25 | + | + |
| 4 | 6 | − | + |
| 5 | 5 | − | − |
| 6 | 5 | − | − |
| 7 | 6 | − | − |
| 8 | 5 | − | + |
| 9 | 5 | − | − |
| 10 | 5 | − | − |
| 11 | 4 | − | − |
| 12 | 6 | − | + |
| 13 | 8 | + | + |
| 14 | 6 | − | − |
| 15 | 5 | − | − |
| 16 | 20 | + | + |
| 17 | 5 | − | + |
| 18 | 5 | − | − |
| 19 | 5 | − | − |
| 20 | 6 | − | + |

From the above, it can be seen that the inventive test compares favorably with known culturing techniques for detecting N. gonorrhoeae.

In order to examine the specificity of the substrate with respect to the enzyme, it was assayed on several analogs of 1,2-propanediol using NAD. Table VI records the results of those tests

TABLE VI

| Substrate | % Reactivity |
|---|---|
| 1,2-propanediol | 100 |
| Glycerol | 1 |
| 1,2 butanediol | 10 |
| 1,3 propanediol | 0 |
| 1,2 ethanediol | 0 |
| 1 chloro 2,3-propanediol | 0 |
| Dihydroxyacetone | 21 |
| Ethanol | 0 |
| 1-propanol | 0 |
| 2-propanol | 0 |
| 1-butanol | 0 |
| Lactic Acid | 0 |

The optimal temperature was determined by monitoring the enzyme activity over a range of temperatures. In general, it was found that some activity is discernible at temperatures approaching 0° C. The activity increases, however, as the temperature is raised with the optimum being at about 50° C.

The operable pH values varied between about 8–11 with the optimum appearing to range between about 9–10.

I claim:

1. A method for detecting the presence of bacteria of the genus Neisseria in a fluid sample, the method comprising testing said sample for an enzyme capable of oxidizing 1,2-propanediol and reducing NAD.

2. A method according to claim 1 wherein the said fluid sample is a lysed human body fluid or exudate and the presence of said enzyme is determined by incubating the sample in a solution of 1,2-propanediol and NAD and determining whether a portion of the NAD is reduced by the lysed sample.

3. The method of claim 2 wherein the reduction is determined fluorometrically.

4. The method of claim 2 wherein the reduction is determined spectrophotometrically.

5. A method of detecting the presence of *Neisseria gonorrhoeae* bacteria in a sample of human body fluid or exudate, the method comprising the steps of contacting the sample with a solution of lysing agent under conditions sufficient to cause the release of intracellular bacterial enzymes thereby forming a lysate and then testing the lysate for the presence of an enzyme capable of oxidizing 1,2-propanediol and reducing NAD.

6. The method of claim 5 wherein the test for the presence of the said enzyme comprises incubating the lysate with a solution of the cofactor nicotinamide-adenine-dinucleotide and 1,2-propanediol and determining whether the cofactor is reduced.

7. The method of claim 6 wherein reduction of the cofactor is determined fluorometrically.

8. The method of claim 6 wherein reduction of the cofactor is determined spectrophotometrically.

* * * * *